United States Patent [19]
Behar et al.

[11] Patent Number: 5,522,274
[45] Date of Patent: Jun. 4, 1996

[54] DEVICE AND PROCESS FOR STUDYING THE BEHAVIOR IN CIRCULATION OF MULTIPHASE EFFLUENTS, APPLICATION TO EFFLUENTS FORMING HYDRATES

[75] Inventors: Emmanuel Behar, Jouy Le Moutier; Maurice Cessou, Saint Symphorien D'Ozon; Choua Cohen, Lyons; Alexandre Rojey; Michel Thomas, both of Rueil Malmaison, all of France

[73] Assignee: Institut Francais du Petrole, Rueil Malmaison, France

[21] Appl. No.: 506,044

[22] Filed: Jul. 24, 1995

Related U.S. Application Data

[63] Continuation of Ser. No. 72,404, Jun. 7, 1993, abandoned.

[30] Foreign Application Priority Data

Jun. 5, 1992 [FR] France .................. 92 06960

[51] Int. Cl.$^6$ .................................................. G01N 33/00
[52] U.S. Cl. .................................. 73/866; 73/61.44
[58] Field of Search ..................... 73/61.44, 61.45, 73/54.12, 432.1, 866, 866.4, 865.6, 861, 3

[56] References Cited

U.S. PATENT DOCUMENTS

| | | | |
|---|---|---|---|
| 3,421,360 | 1/1969 | Luse et al. | 73/3 |
| 3,464,637 | 9/1969 | Siewert | 73/866 X |
| 3,580,045 | 5/1971 | Pfrehm | 73/3 |
| 4,381,665 | 5/1983 | Levine et al. | 73/153 X |
| 4,606,218 | 8/1986 | Chisman, III | 73/3 |
| 4,852,395 | 8/1989 | Kolpak | 73/61.44 |
| 5,239,862 | 8/1993 | Atkinson | 73/61.44 |
| 5,251,488 | 10/1993 | Haberman et al. | 73/61.44 X |

FOREIGN PATENT DOCUMENTS

| | | | |
|---|---|---|---|
| 0337821 | 10/1989 | European Pat. Off. | |
| 0435713 | 7/1991 | European Pat. Off. | |
| 295713 | 11/1991 | Germany | 73/866 |
| 1530907 | 12/1989 | U.S.S.R. | 73/866 |
| 1557482 | 4/1990 | U.S.S.R. | 73/866 |

OTHER PUBLICATIONS

Measurements, vol. 3, No. 1, Jan./Mar. 1985, pp. 7–14; M. S. Beck, et al "On–Line Measurement of Oil/Gas/Water Mixtures Using a Capacitance Sensor".

*Primary Examiner*—Thomas P. Noland
*Attorney, Agent, or Firm*—Antonelli, Terry, Stout & Kraus

[57] ABSTRACT

A device for studying the behavior of a multiphase effluent in circulation includes a test pipe having two ends containing the effluent and a unit for delivering a working fluid alternately into each end of the pipe to effect movement of the effluent. The effluent to be studied which has been placed in the test pipe, is displaced according to an alternating circulation generated by injection of a working fluid into each of the ends of the pipe. A process for studying the behavior of the multiphase fluid in circulation involves placing the effluent in a test pipe, displacing the effluent in the test pipe in an alternating motion by delivering a working fluid alternately into each end of the pipe and measuring behavior of the effluent during the alternating displacement of the effluent.

16 Claims, 4 Drawing Sheets

DEVICE AND PROCESS FOR STUDYING THE BEHAVIOR IN CIRCULATION OF MULTIPHASE EFFLUENTS, APPLICATION TO EFFLUENTS FORMING HYDRATES

This application is a continuation application of application Ser. No. 072,404, filed Jun. 7, 1993 and now abandoned.

BACKGROUND OF THE INVENTION

The present invention relates to a device and to a process for studying the behaviour, in circulation, of a multiphase effluent. A multiphase effluent is understood to be an effluent which may comprise several phases, notably a gas, liquid or solid phase.

Since it is not possible, for economic reasons, to study the circulation of multiphase effluents in real-size pipes which may be several kilometers long, it is necessary to build a simulation plant comprising a pipe fraction of limited size in which the effluent to be studied is circulated.

It is well-known to set up a simulation loop in which the effluent to be studied is circulated. But since the circulating means do not always work properly in the presence of a multiphase effluent containing a relatively considerable gas phase, the loop is equipped with two circulating means, one specialized for liquids, the other for gases. Of course, the multiphase effluent must be subjected to a stage of separation between the liquid and the gas phase before it is fed separately into each of the circulating means. This system has many drawbacks:

at each cycle, the gases are separated from the liquids, then they are mixed together. The effluent is thus continuously homogenized.

The pump and the compressor stir the phases and segregation processes during the transport of the effluent are concealed.

The mechanical stirring of the liquids by the pump may change the rheologic properties of the effluent.

The pump may generate crushing of the solid phases.

The pump undergoes abrasion through the solids. Besides, the abrasion products may soil the effluent tested and change the physicochemistry of the flow.

SUMMARY OF THE INVENTION

The present invention thus relates to a device for studying the behaviour of a multiphase effluent in circulation. It comprises a test pipe containing said effluent, means suited for delivering a fluid alternately into each of the ends of said pipe.

The pipe and the means may have a relative lay-out suited for substantially limiting the mixing of the effluent with the fluid.

The means may comprise at least one piston driven by an alternating motion in a liner communicating with at least one end of the pipe.

The means may comprise a pumping means and distribution means, and the distribution means may control the delivery of the fluid alternately towards one, then the other end of said test pipe.

The means may comprise an alternating circulation means comprising two cylinders and two identical pistons, said pistons being connected together mechanically by a rod and delimiting in each cylinder a front chamber and a rear chamber on the rod side. The two identical chambers may communicate each with an end A or B, and the two other chambers may communicate with said distribution means.

The fluid may have substantially the composition of the gas phase contained in said multiphase effluent.

The fluid may mainly comprise the fluid of higher density contained in said effluent.

The device may comprise at least one system allowing fluid supply in the delivery circuit.

The device may comprise at least one system allowing fluid supply in said test pipe.

The test pipe may be equipped with means for regulating the temperature of the effluent, means for measuring and/or for controlling the behaviour of the effluent.

The invention further relates to a process for studying the behaviour of a multiphase effluent in circulation, comprising the following stages:

placing said effluent into a test pipe, displacing said effluent in the pipe, in an alternating motion, by delivering a fluid alternately into each end of said pipe, controlling and/or measuring the behaviour of said effluent during said alternating displacement.

The flow rate of the effluent in the pipe may be adjusted notably by acting on the rate of delivery of the fluid.

The pressure of the effluent in the pipe may be adjusted by acting on the pressure of the fluid through appropriate means.

The fluid used may be a gas whose composition is close to that of the gas phase of said effluent and the temperature of the effluent in the pipe may be regulated.

The device and the process described above may be applied to the study of the behaviour of a multiphase effluent circulating in a pipe.

Processes for delaying the formation and/or for reducing the susceptibility to agglomeration of hydrates formed during the transport of said effluent may be tested and/or studied.

The basic idea of the invention is to subject a determined volume of a multiphase effluent to an alternating displacement in a test pipe. Displacement may be achieved over a distance and during a time simulating transport conditions by circulation in industrial pipes. The influence of the length of industrial pipes is expressed by the effect of the residence time of the effluents displaced in the test pipe.

The present invention mainly has the following advantages:

no separation of the various phases during the total simulated industrial flow.

No homogenization of the phases is generated by the circulation means. The natural evolution of the system may thus be studied. In fact, when the action of certain additives (for example anticorrosive additives, bactericides, dispersers, . . . ) is to be tested, it is essential not to mix continuously the effluent with the additives so as to remain as close as possible to the industrial conditions where such mixing does not occur. The alternating displacement mode of the present invention does therefore not conceal the possible segregation effects which may take place in the industrial pipe between the various products.

The fact that the effluent does not pass through a pump or equivalent avoids any shearing of the fluids and of the solids present. Thus, the evolution of the rheologic properties of the multiphase effluent circulating in the pipe is not modified.

If the effluent is laden with solid particles, the alternating motion respects the distribution of these particles between the various phases, as well as their possible decantation or segregation.

The solid particles contained in the effluent undergo no morphological transformation.

Various multiphase effluents may be studied in the device according to the invention. They may notably be:

a liquid-gas mixture : the gas phase may be a pure gas or a gas mixture representing preferably a natural gas. The compounds belonging to this category may notably be methane, ethane, propane, n- or i-butane, $CO_2$ or $H_2S$. The liquid phase may consist of pure or salt water comprising additives, for example hydrate inhibitors such as methanol or a glycol.

A liquid-gas mixture such as defined above, with a second liquid phase, for example a natural gas condensate or a crude oil.

A liquid-gas-solid mixture: the liquid and the gas phase may be the effluents described above, in which the solid phase consists of gas hydrates.

A liquid mixture consisting mainly and notably of water and of liquid hydrocarbons.

A liquid-solid mixture: the liquid phase mainly consists of water saturated with dissolved hydrocarbon gas, possibly comprising liquid hydrocarbons. The solid phase consists of gas hydrates.

In each of the previous cases, additives (for example anticorrosive additives, bactericides, dispersers, . . . ) may be added to the multiphase effluent studied.

The effluents described above are given by way of example of a particular application of the device and of the process according to the invention concerning the study of effluents forming gas hydrates. The present invention is not limited to these particular effluents.

The formation of hydrates is dreaded, notably in the petroleum and gas industry where the hydrates formation conditions are often combined. These hydrates form when the water is in the presence of the gas, either in the free state or dissolved in a liquid phase, such as a liquid hydrocarbon, and when the temperature reached by the mixture becomes lower than the thermodynamic temperature of hydrates formation. The gases, such as natural gas, petroleum gas or other gases, which form the hydrates with water may notably comprise, for example, methane, ethane, ethylene, propane, propene, n-butane, i-butane, $H_2S$, $CO_2$.

The formation of hydrate plugs may lead to production stop and therefore bring about considerable financial losses.

The present invention is particularly well-suited for studying the formation of hydrates and/or remedies to be applied.

The present invention is not limited to this particular application. In fact, its advantages and qualities are relevant for all studies concerning multiphase flows in general.

BRIEF DESCRIPTION OF THE DRAWINGS

Other features and advantages of the present invention will be clear from reading the description hereafter given by way of particular, non limitative examples, with reference to the accompanying drawings in which.

DESCRIPTION OF THE PREFERRED EMBODIMENTS

Figure 1:
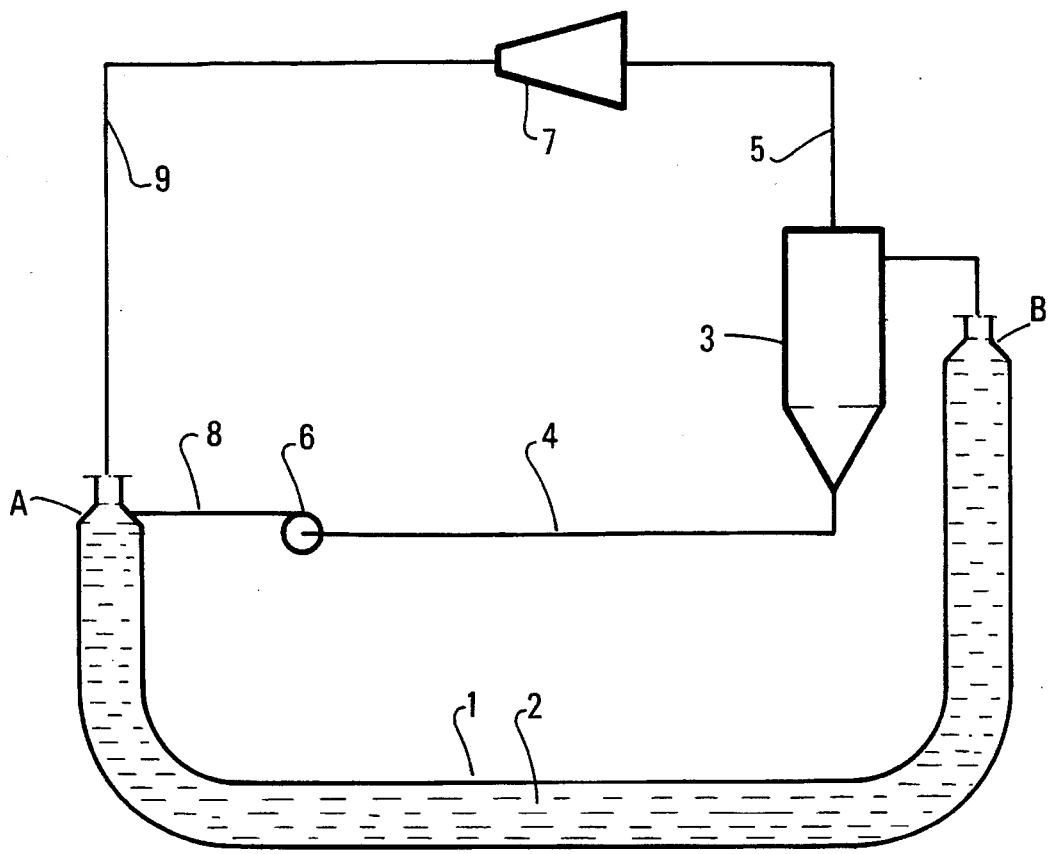
FIG. 1 is a diagram of a simulation circulation loop according to the prior art, FIG. 2 describes the principle of the invention according to a particular embodiment.

FIG. 1 illustrates the prior art in which a simulation circulation loop comprises a pipe 1 with its two ends referenced A and B. Between A and B, the pipe is filled with the multiphase effluent 2. The effluent circulates from A to B. Downstream from B, said effluent flows into a separator 3. The liquid or the liquids, laden with solids or not, are discharged through line 4 and fed to the inlet of a pump 6. In separator 3, the gas phase is discharged through line 5 towards a compressor 7.

The two delivery means, pump 6 and compressor 7, deliver the fluids respectively into pipes 8 and 9, upstream from the end A of the pipe where the fluids mix together before circulation in pipe 1.

The drawbacks of this architecture have already been detailed above.

Figure 2:
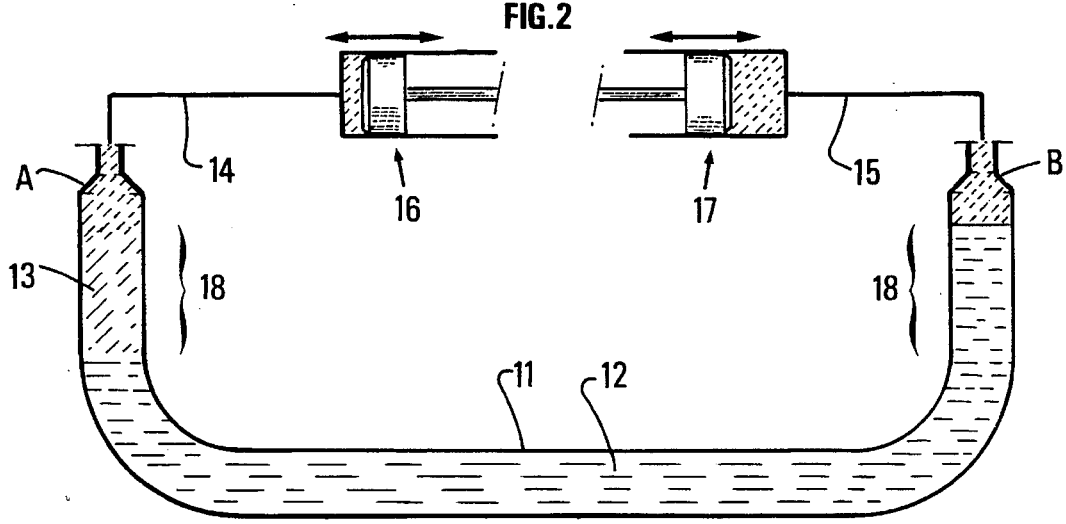

FIG. 2 shows the principle according to the invention of the alternating circulation of a multiphase effluent 12 in a test pipe 11 having one end A and another end B.

The two ends A and B of the pipe are connected fluidically, respectively through pipes 14 and 15, to delivery or circulation means 16 and 17. Pipes 14 and 15 are filled with a fluid 13. The delivery means 16 and 17 are illustrated here by piston/cylinder assemblies. The displacements of the two pistons are synchronized with each other, either by means of a mechanical transmission, or through the construction of a double-effect delivery assembly, or by an external synchronization control system, for example by means of sensors for picking up the displacement of the pistons of means 16 and 17.

The working principle is the following: when means 16 delivers the fluid 13 into pipe 14, effluent 12 is pushed forward. The interface between fluid 13 and effluent 12, located on end A side, moves as a function of the volume of fluid 13 delivered by means 16. At the same time, the interface between the two fluids, on end B side, is displaced in the same direction, which pushes the same volume of fluid into means 17 which performs then its suction cycle. The displacements of means 16 and 17 are then reversed, which displaces effluent 12 in the opposite direction, that is from B to A. The interfaces between the working fluid and the multiphase fluid to be studied move along the path illustrated in FIG. 2 by reference 18.

The displacement length 18 is set by the volume of fluid 13 delivered, and the displacement speed of effluent 12 is set by the delivery speed of said means 16 and 17 or by their rate of delivery.

Fluid 13 may be liquid or gaseous. The delivery means 16 and 17 will of course be suited to the nature of the working fluid. In order to avoid any substantial change in the composition of effluent 12 during its alternating displacement in pipe 11, a gaseous working fluid will be preferably selected, of a composition close to the gas phase contained in multiphase effluent 12. If the working fluid is liquid, it will also preferably have a composition close to the densest liquid of the effluent.

Furthermore, in order to limit the mixing of the working fluid in the effluent, the lay-out of pipe 11 with respect to pipes 14, 15 and to the delivery means will be such that the distribution of the two fluids, notably through the segregation process, induces practically no mixing. In fact, if the density of the working fluid is lower than that of the effluent, pipe 11 will be preferably located at a lower level with respect to the equipments containing the working fluid. On the other hand, if the density of the effluent is lower than that of the working fluid, pipe 11 will be preferably arranged above pipes 14 and 15, and possibly above the delivery means comprising the working fluid. It should be noted that the object of the lay-out of test pipe 11 with respect to the pipes and equipments containing the working fluid is mainly to limit the mixing of the fluids in contact. The present invention may comprise all the lay-outs and shapes of pipes 14 and 15 avoiding penetration of one of the fluids into a pipe containing the other fluid. For example, pipes 14 and 15 may have upper or lower points, according to the density of the working fluid, or the device may comprise separation means, such as mobile pistons, separating physically the various fluids.

Figure 3:
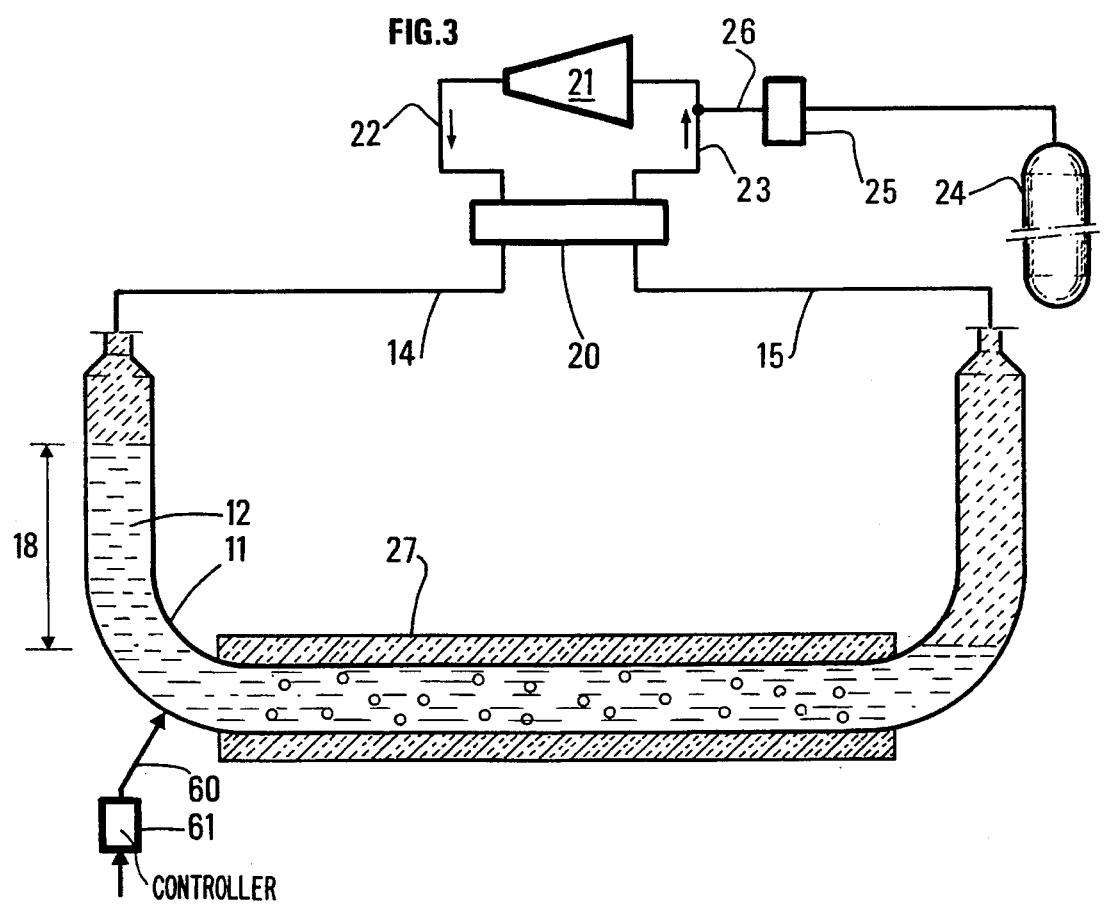
FIG. 3 illustrates the invention according to a preferred embodiment.

FIG. 3 illustrates a preferred embodiment of the device according to the invention. Test pipe 11, filled with the effluent to be studied 12, is connected by pipes 14 and 15 to a distribution means 20. Delivery means 21 is connected to distribution means 20 by a delivery pipe 22 and by a suction pipe 23. Suction pipe 23 comprises an inlet of another pipe 26 allowing adjustment of the volume and of the pressure of the working fluid. Pipe 26 is connected to a tank 24 containing a working fluid, and comprises a control device 25. In case of a gaseous working fluid, this device 25 is for example a valve equipped with a pressure regulator. In case of a liquid fluid, that is little compressible, there may notably be a fluid transfer means equipped with a valve. A pipe 60 comprising a control means 61 opens into test pipe 11. Control means 61 allows fluid to be supplied into or withdrawn from the test pipe. Multiphase effluent may thus be added, withdrawn, or mixed into the additives test pipe.

The function of distribution means 20 is to alternately drive the working fluid delivered through pipe 22 towards pipe 14 and then towards pipe 15, and at the same time to connect pipe 15, then pipe 14 to return pipe 23. Thus, the alternating displacement of fluid 12 will be obtained through distribution means 20.

Pipe 11 may comprise a temperature regulation system 27 and a set of measuring and control devices, notably absolute or differential pressure sensors, flow rate sensors, analyzers of the various phases, densimeters or means for displaying the flow of the effluent in the pipe.

Moreover, resistivity sensors may be used to detect the position of the effluent/working fluid interface. The distribution means may thus be controlled so as to invert the direction of the flows when these sensors show that the effluent front has reached the extreme position.

Such a device allows the amplitude of the displacement shown by arrow 18 to be adjusted notably during the time of alternation given by the distribution means for a given flow rate of delivery means 21. The velocity of flow, and thus the rate of flow of the effluent, is directly related to the flow rate of delivery means 21.

The advantage of the embodiment according to FIG. 3, with respect to the embodiment of FIG. 2, is notably not to set in alternating motion mechanical parts of high inertia, for example pistons, but only distribution elements generally more suited to such a running.

Figure 3A:
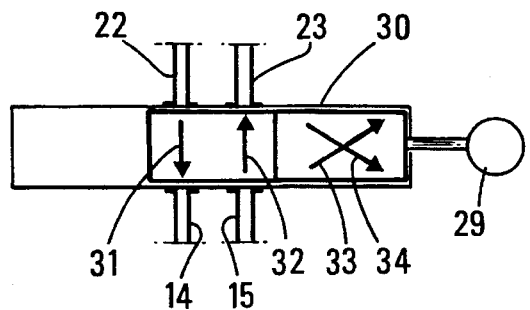
FIG. 3A illustrates an embodiment of the distribution means of the device according to the invention.

FIG. 3A illustrates the main function of distribution means 20, that is a flow rate inversion or crossing. The components intended to fulfil this function are well-known in the distribution technique of fluids, be they compressible or practically incompressible. This function is shown here by a slide valve distributor 30 which may take two positions by means of motor means 29.

In the position of FIG. 3A, the working fluid delivered through pipe 22 is driven as shown by arrow 31 into the pipe 14 connected to one end of the test pipe. The working fluid of pipe 15, driven by effluent 12, is fed as shown by arrow 32 towards the pipe 23 connected to the inlet of the delivery means. When motor means 29 is activated so as to push slide valve 30 to the left of FIG. 3A, the working fluid of pipe 22 is fed as shown by arrow 34 towards pipe 15, while the fluid contained in pipe 14 is fed as shown by arrow 33 towards inlet pipe 23. Upon each displacement of slide valve 30, the direction of displacement of the working fluid is inverted and the direction of flow of the effluent in the test pipe is therefore also inverted. Without departing from the scope of this invention, the distribution means may comprise at least a third position, generally intermediate between the two described above. The third position may notably provide direct communication between pipes 22 and 23, or total sealing of pipes 22 and 23. The communications internal to slide valve 30 may also be so designed that displacement of the slide valve generates little or no overpressure, particularly if the working fluid is practically incompressible.

Figure 3B:
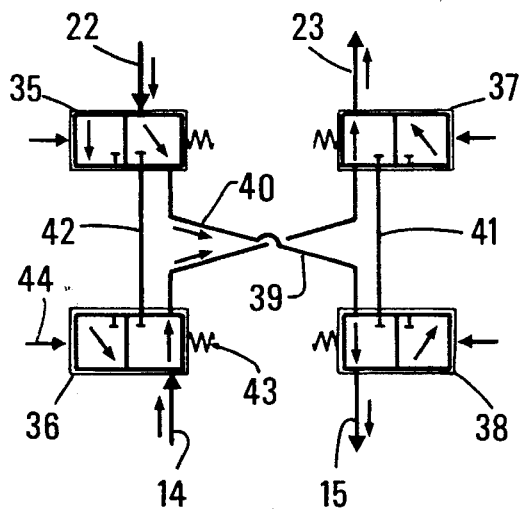
FIGS. 3B and 3C illustrate another embodiment of the distribution means.
Figure 3C:
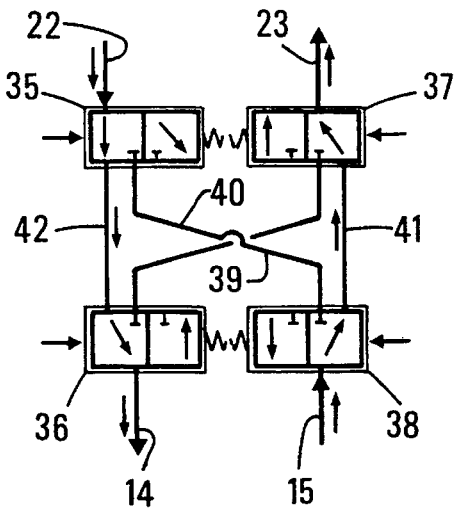

FIGS. 3B and 3C show another embodiment of distribution means 20 where valves or distributors having three ports and two positions are used. FIG. 3B illustrates the conditions of the distributors so as to have one direction of flow, FIG. 3C illustrates the conditions for the other direction of flow.

FIG. 3B shows the respective position of the four valves 35, 36, 37 and 38 so that the working fluid delivered through pipe 22 is fed into pipe 15 connected to one end of the test pipe, and so that the working fluid driven back from the test pipe into pipe 14 may come back to the suction pipe 23 connected to the delivery means. Four pipes 39, 40, 41 and 42 connect the four valves together. The arrows in FIG. 3B show clearly the directions of circulation of the working fluid. No fluid circulates in pipes 41 and 42 which are sealed in this first position of distributors 35, 36, 37 and 38.

FIG. 3C shows the same embodiment when the four valves or distributors 35, 36, 37 and 38 occupy their second position. The working fluid is then driven from pipe 22 towards pipe 14 connected to the other end of the test pipe. The fluid in pipe 15 is driven at the same time towards suction pipe 23. In this configuration, the working fluid circulates through pipes 41 and 42, whereas pipes 39 and 40 are sealed.

References 43 and 44 relate to the means for motorizing valve 36, the means for motorizing valves 35, 37 and 38 being identical. This motorization may comprise one of means 44 known in the profession, for example a hydraulic, pneumatic or electric means with return means 43.

Figure 5:
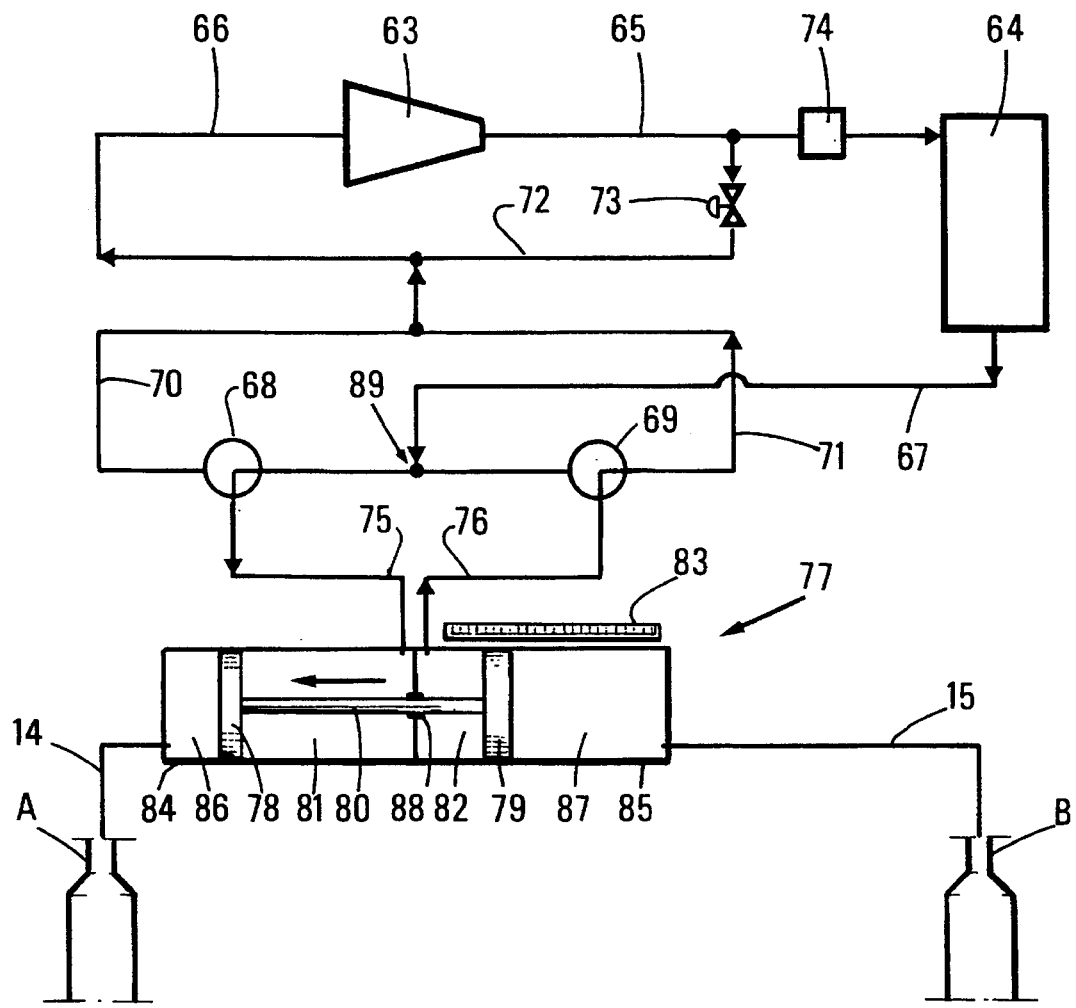
FIG. 5 shows another preferred embodiment of the test loop.

FIG. 5 shows another preferred embodiment of the device in which the test loop is connected through pipes 14 and 15 to an alternating circulation means 77. This means comprises two pistons 78 and 79 connected together by a rod 80.

These two pistons slide longitudinally into two liners 84 and 85 of equal axis. A sealed bearing 88 separates chambers 81 and 82 tightly on the piston rod side. The front chambers 86 and 87 communicate respectively with the ends A and B of the test loop through pipes 14 and 15.

Chambers 81 and 82 are connected through pipes 75 and 76 to a distribution system comprising valves 68 and 69.

A delivery means 63 sucks in a fluid from pipe 66 and feeds it into pipe 65. The fluid delivered transits through an exchanger 64 before it reaches point 89 through pipe 67. Point 89 admits the fluid delivered at the inlet of the two valves 68 and 69. The return fluid is collected through pipes 70 and 71 towards the inlet of delivery means 63 through pipe 66. A flow rate sensor 74 controls the running of delivery means 63 and allows adjustment of the displacement speed of the coupling of pistons 78 and 79. A safety valve 73, normally closed, informs about an accidental pressure build-up in the delivery circuit by bypassing the delivery and inlet of the pumping means 63 when the pressure reaches a maximum value.

An array 83 of sensors for picking up the position of the coupling of pistons 78 and 79 allows the length of the displacement to be adjusted, adjusting thereby the amplitude of the alternating circulation.

The device according to the embodiment of FIG. 5 works as follows:

valve 68 is shown here in the position of admission of the fluid delivered into chamber 81, the fluid under pressure pushes piston 78 to the left of the figure, driving back the fluid contained in chamber 86, pipe 14 drives the fluid towards the end A of the pipe, at the same time, valve 69 drives the fluid contained in chamber 82 towards the inlet of the delivery means through pipes 71 and 66, when piston 79 has ended its travel, it releases a sensor indicating the end of travel of array 83, the end-of-travel sensor controls the paired reversal of the positions of the two valves 68 and 69, admission and return invert, thereby inverting the displacement of the piston towards the right of the figure, the fluid is then fed to the end B of the test loop, a cycle ends when piston 79 releases the other end of travel.

The advantage of such an embodiment is notably to have a displacement fluid circuit physically insulated from the fluids contained in the test loop. Moreover, it is also possible to use a fluid delivered through means 63, different from the fluid contained in pipes 14 and 15, a fluid which is contact with the effluent. Besides, the pressures prevailing on either side of pistons 78 and 79 may be different since the circuits are separate. This embodiment also provides easy control of the alternation of circulation by position sensors controlling the displacement of a piston, which is easier and more precise than the detection of an interface between two fluids.

Of course, the same fluid may be utilized in the various chambers of circulator 77 without departing from the scope of this invention.

The present invention is not limited to the embodiments described here of distribution means 20. In fact, any other system for inverting the flow rates, suited for running alternately, may be suitable for the process and the device according to the invention.

Figure 4:
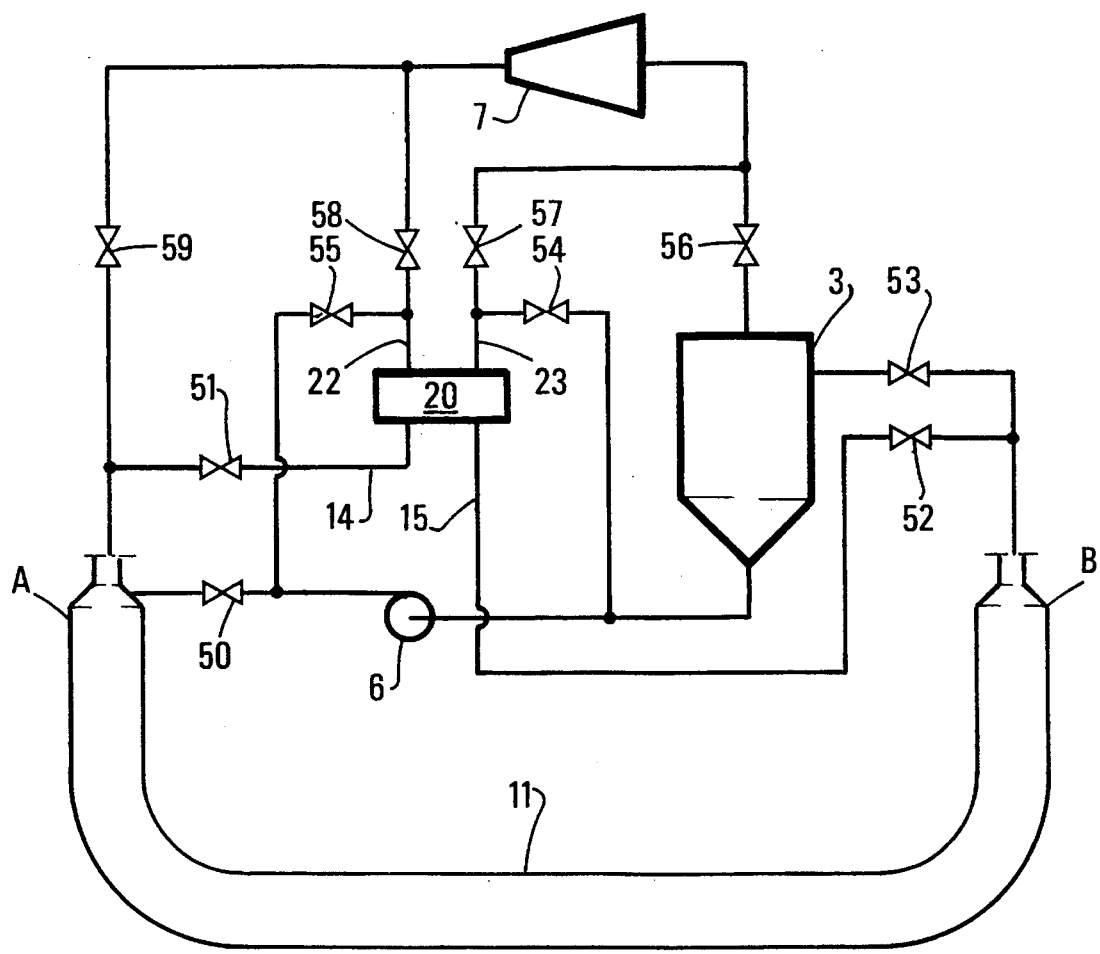
FIG. 4 illustrates an embodiment of the device according to the invention in which the simulation loop according to the prior art is integrated.

FIG. 4 illustrates a lay-out of a device according to the invention in which a circulation loop according to the prior art (FIG. 1) is advantageously integrated.

This device comprises:

a test pipe 11 comprised between two ends A and b, two delivery means: a compressor 7 and a hydraulic pump 6, a distribution means 20, a liquid/gas separator 3, an array of pipes connecting fluidically the various components, an array of valves 50, 51, 52, 53, 54, 55, 56, 57, 58 and 59 allowing the fluids to be driven according to the desired configuration.

The test device according to the diagram of FIG. 4 may work according to three modes : 1) According to the prior art; 2) In alternating circulation with a gaseous working fluid; 3) In alternating circulation with a liquid working fluid.

1) According to the prior art:

Valves 51, 52, 54, 55, 57 and 58 are closed.

Valves 50, 53, 56 and 59 are open.

The effluent circulates according to the description above of FIG. 1.

2) In alternating circulation with a gaseous working fluid:

Valves 50, 53, 54, 55, 56 and 59 are closed.

Valves 51, 52, 57 and 58 are open.

The separator 3 and the hydraulic pump 6 are insulated from the circulation circuit of the working fluid and the distribution means is in operation to distribute the gas delivered by compressor 7 in pipe 22, alternately towards pipe 14 then 15. The circulation of the effluent contained in test pipe 11 occurs in the alternating mode according to the present invention.

3) In alternating circulation with a liquid working fluid:

Valves 50, 53, 56, 57, 58 and 59 are closed.

Valves 51, 52, 54 and 55 are open.

Separator 3 and compressor 7 are insulated from the circuit and pump 6 delivers the working fluid into pipe 22, its inlet being connected to pipe 23.

We claim:

1. A device for studying the behavior of a multiphase effluent in circulation, comprising a test pipe having two ends containing said effluent and means for delivering a monophasic working fluid alternately into each of the ends of said pipe to effect movement of the effluent.

2. A device as claimed in claim 1, wherein said means for delivering a monophasic working fluid comprise a pumping means and distribution means, and wherein said distribution means control the delivery of the working fluid alternately towards one end, and then towards the other end of said test pipe.

3. A device as claimed in claim 1, wherein said device comprises at least one system allowing supply of the working fluid in a delivery circuit connected alternately to one of the ends of the test pipe.

4. A device as claimed in claim 1, wherein said device comprises at least one system allowing supply of additional effluent to the effluent in said test pipe.

5. A device as claimed in claim 1, wherein said test pipe is equipped with means for regulating the temperature of the effluent, and means for measuring the behavior of the effluent.

6. A device for studying the behavior of a multiphase effluent in circulation, comprising a test pipe having two ends containing said effluent and means for delivering a monophasic working fluid alternately into each of the ends of said pipe to effect movement of the effluent; said pipe and said means for delivering a monophasic working fluid having a relative arrangement suited for substantially limiting the mixing of the effluent with the working fluid.

7. A device as claimed in claims 1 or 6, wherein said means for delivering said monophasic working fluid comprise at least one piston driven by an alternating motion in a liner communicating with at least one end of the pipe.

8. A device for studying the behavior of a multiphase effluent in circulation, comprising a test pipe having two ends containing said effluent and means for delivering a monophasic working fluid alternately into each of the ends of said pipe to effect movement of the effluent; said means for delivering a monophasic working fluid comprising a pumping means and a distribution means, said distribution means controlling the delivery of the working fluid alternately towards one end and then towards the other end of said test pipe and said means for delivering a monophasic working fluid comprise an alternating circulation means comprising two cylinders and two identical pistons, said pistons being mechanically connected by a rod and delimiting in each cylinder a front chamber and a rear chamber on the rod side, and wherein two identical front chambers communicate each with an end of the test pipe, the two other chambers communicating with said distribution means.

9. A device for studying the behavior of a multiphase effluent in circulation, comprising a test pipe having two ends containing said effluent and means for delivering a monophasic working fluid alternately into each of the ends of said pipe to effect movement of the effluent; said working fluid comprising a monophasic fluid which has substantially the same composition as a gas phase contained in said multiphase effluent.

10. A device for studying the behavior of a multiphase effluent in circulation, comprising a test pipe having two ends containing said effluent and means for delivering a monophasic working fluid alternately into each of tile ends of said pipe to effect movement of the effluent; said working fluid comprising mainly a single phase fluid of higher density contained in said effluent.

11. A process for studying the behavior of a multiphase effluent in circulation, comprising the following steps:

placing said effluent in a test pipe having two ends, displacing said effluent in the test pipe, in an alternating motion, by delivering a monophasic working fluid alternately in each end of said pipe, and measuring the behavior of said effluent during said alternating displacement of the effluent.

12. A process as claimed in claim 11, wherein the flow rate of the effluent in the pipe is adjusted by acting on the rate of delivery of the working fluid.

13. A process as claimed in claim 11, wherein the pressure of the effluent in the pipe is adjusted by means acting on the pressure of the working fluid.

14. A process for studying the behavior of a multiphase effluent in circulation, comprising the following steps:

placing said effluent in a test pipe having two ends, displacing said effluent in the test pipe, in an alternating motion, by delivering a monophasic working fluid alternately in each end of said pipe, and measuring the behavior of said effluent during said alternating displacement of the effluent; the working fluid being a gas whose composition is close to that of a gas phase of said effluent and the temperature of the effluent in the pipe being regulated.

15. A process for studying the behavior of a multiphase effluent in circulation, comprising the following steps:

placing said effluent in a test pipe having two ends, displacing said effluent in the test pipe, in an alternating motion, by delivering a monophasic working fluid alternately in each end of said pipe, and measuring the behavior of said effluent during said alternating displacement of the effluent; wherein a process for delaying the formation and/or for reducing the susceptibility to agglomeration of hydrates formed during the transport of said effluent is studied.

16. A process for studying the behavior of a multiphase effluent in circulation, comprising the following steps:

placing said effluent in a test pipe having two ends, displacing said effluent in the test pipe, in an alternating motion, by delivering a monophasic working fluid alternately in each end of said pipe, and measuring the behavior of said effluent during said alternating displacement of the effluent; the flow rate of the effluent in the pipe being adjusted by acting on the rate of delivery of the working fluid, the working fluid being a gas whose composition is close to that of a gas phase of said effluent and the temperature of the effluent in the pipe being regulated.

* * * * *